US010890573B2

(12) United States Patent
Kuczynski et al.

(10) Patent No.: US 10,890,573 B2
(45) Date of Patent: Jan. 12, 2021

(54) FACILE METHODS TO DETECT TOXIN IN SEAFOOD

(71) Applicant: International Business Machines Corporation, Armonk, NY (US)

(72) Inventors: Joseph Kuczynski, North Port, FL (US); Marvin M. Misgen, Rochester, MN (US); Debra A. Neuman-Horn, Rochester, MN (US); Kevin J. Przybylski, Rochester, MN (US); Joseph F. Prisco, Rochester, MN (US); Brandon M. Kobilka, Tucson, AZ (US)

(73) Assignee: International Business Machines Corporation, Armonk, NY (US)

( * ) Notice: Subject to any disclaimer, the term of this patent is extended or adjusted under 35 U.S.C. 154(b) by 351 days.

(21) Appl. No.: 15/846,406

(22) Filed: Dec. 19, 2017

(65) Prior Publication Data

US 2019/0187117 A1 Jun. 20, 2019

(51) Int. Cl.
*G01N 21/82* (2006.01)
*G01N 33/12* (2006.01)
*G01N 21/78* (2006.01)

(52) U.S. Cl.
CPC ............. *G01N 33/12* (2013.01); *G01N 21/78* (2013.01); *G01N 21/82* (2013.01); *G01N 2333/43504* (2013.01); *G01N 2333/4603* (2013.01)

(58) Field of Classification Search
CPC ........ G01N 21/82; G01N 21/83; G01N 33/12; G01N 2333/43504; G01N 2333/4603
See application file for complete search history.

(56) References Cited

U.S. PATENT DOCUMENTS 5,525,525 A 6/1996 Hokama
6,270,982 B1 * 8/2001 Jordan ................ G01N 33/579 424/184.1

(Continued)

FOREIGN PATENT DOCUMENTS

WO 2012046563 A1 4/2012

OTHER PUBLICATIONS

Beklemishev, M.K. et al. "Radical polymerization as an indicator reaction for determination of organic compounds," Moscow University Chemistry Bulletin, 2007, vol. 62, No. 6, pp. 335-342. Original Russian Text published in Vestnik Moskovskogo Universiteta. Khimiya, 2007, No. 6, pp. 407-417. (Year: 2007).*

(Continued)

*Primary Examiner* — Christopher Adam Hixson
*Assistant Examiner* — Michelle Adams
(74) *Attorney, Agent, or Firm* — Patterson + Sheridan, LLP

(57) ABSTRACT

Methods and systems for detecting environmental contaminants is described. In an embodiment, a method includes macerating and extracting a sample; reacting a first polymerizable compound with the sample to form a second mixture comprising a second polymerizable compound; adding an initiator to the second mixture comprising the second polymerizable compound; performing a polymerization reaction on the second mixture comprising the second polymerizable compound to form a third mixture comprising a precipitate; and performing a turbidimetric analysis on the third mixture comprising the precipitate. In another embodiment, a method includes macerating and extracting a sample; reacting a first mixture comprising the functionalized polythiophene compound and the sample to form a second mixture comprising a second functionalized polythiophene compound; performing a colorimetric analysis on (Continued)

the second mixture comprising the second functionalized polythiophene compound.

20 Claims, 10 Drawing Sheets

(56) References Cited

U.S. PATENT DOCUMENTS

| | | | |
|---|---|---|---|
| 6,652,807 | B1 | 11/2003 | Ebesu et al. |
| 7,399,470 | B2 | 7/2008 | Hirama et al. |
| 8,599,382 | B2 | 12/2013 | Pierce, Jr. et al. |
| 9,029,082 | B2 | 5/2015 | Friedberger et al. |
| 2011/0065138 | A1 | 3/2011 | Botana Lopez et al. |
| 2016/0161490 | A1 | 6/2016 | Fujita |
| 2016/0281178 | A1 | 9/2016 | Medlin et al. |

OTHER PUBLICATIONS

Aldrich Chemical Co "Applications: Free Radical Initiators. Thernnal Initiators: Decomposition Rate and Half-Life." <www.sigmaaldrich.com/content/dam/sigma-aldrich/docs/Aldrich/General_Information/thermal_initiators.pdf?utm_source=redirect&utm_medium=promotional&utm_campaign=insite_thermal_initiators> (Year: 2011).*

Georgieff, K.K. "Relative Inhibitory Effect of Various Compounds on the Rate of Polymerization of Methyl Methacrylate," Journal of Applied Polymer Science, vol. 9, pp. 2009-2019 (1965) (Year: 1965).*

Kaastrup, K. et al. "Using photo-initiated polymerization reactions to detect molecular recognition," Chem. Soc. Rev., 2016, 45, 532-545. (Year: 2016).*

Wu, Y. et al. "Target-Triggered Polymerization for Biosensing," Accounts of Chemical Research vol. 45, No. 9, 2012, pp. 1441-1450. (Year: 2012).*

Lou, X. et al. "Radical polymerization in biosensing," Anal Bioanal Chem (2006) 386: 525-531. (Year: 2006).*

Caillaud et al, "Update on Methodologies Available for Ciguatoxin Determination: Perspective to Confront the Onset of Ciguatera Fish Poisoning in Europe," Mar. Drugs 2010,87,1838-1907; 70 pages.

Bovee et al, "Tailored Microarray Platform for the Detection of Marine Toxins," dEnviron. Sci. Technol. 2011, 45, 8965-8973.

Malki et al, Liquid Chromatography—Mass Spectrometry in Food Safety, Journal of Chromatopgraphy A, 1217, (2010), 4018-4040.

* cited by examiner

305

315

325

701 (P1)

702 (P2)

703 (P3)

704 (P4)

701' (P1')

702' (P2')

703' (P3')

704' (P4')

FACILE METHODS TO DETECT TOXIN IN SEAFOOD

BACKGROUND

The present disclosure relates to methods for detecting a target substance and, more specifically, methods to detect toxins such as ciguatera in fish and aquatic invertebrates.

Ciguatera is a form of food poisoning caused by toxins produced by dinoflagellates, a large group of protists that occur in marine and fresh water habitats. The toxins accumulate in the tissues of fish and invertebrates that eat the dinoflagellates and produce the poisoning when they, in turn, are consumed by humans and other animals. Ciguatoxins are extremely toxic and resistant to heat and cold, so cooking or freezing the seafood does not eliminate the toxin. Annual ciguatera cases worldwide are estimated to be at least 50,000.

The most common test available for detecting ciguatera in fish is the mouse bioassay. These mouse bioassays are complicated and can take more than four days to obtain results. Other conventional detection methods for ciguatoxin include biochemical assays (such as ELISA, radiochemical assays, and monoclonal antibody assays), and chemical assays (such as chromatographic detection, nuclear magnetic resonance (NMR), mass spectrometry (MS) assays). However, none of these are amenable to rapid detection of the toxin in a food preparation environment (e.g., the kitchen of a restaurant or the stock room of a grocer). Consequently, a facile detection method for ciguatoxin in these environments is highly desirable.

SUMMARY

According to an embodiment, a method for detecting a target substance is provided. The method includes macerating a sample and extracting the sample; providing a first mixture comprising the sample and a first polymerizable compound comprising a substituent that reacts with a primary hydroxyl group; reacting the first polymerizable compound with the sample to form a second mixture comprising a second polymerizable compound; adding an initiator to the second mixture comprising the second polymerizable compound; performing a polymerization reaction on the second mixture comprising the second polymerizable compound to form a third mixture comprising a precipitate; and performing a turbidimetric analysis on the third mixture comprising the precipitate.

According to an embodiment, a method for detecting a target substance is provided. The method includes macerating a sample and extracting the sample; providing a first mixture comprising the sample and a first functionalized polythiophene comprising a substituent that reacts with a primary hydroxyl; reacting the first mixture comprising the functionalized polythiophene compound and the sample to form a second mixture comprising a second functionalized polythiophene compound; performing a colorimetric analysis on the second mixture comprising the second functionalized polythiophene compound.

According to another embodiment, a system to detect a target substance is provided. The system includes a first compound comprising a multifunctional monomer compound, a functionalized polythiophene compound, or a combination thereof; and one or more of a solvent or an extraction solvent.

Features and other benefits that characterize embodiments are set forth in the claims annexed hereto and forming a further part hereof. However, for a better understanding of the embodiments, and of the advantages and objectives attained through their use, reference should be made to the Drawings and to the accompanying descriptive matter.

BRIEF DESCRIPTION OF THE SEVERAL VIEWS OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, for the disclosure may admit to other equally effective embodiments.

DETAILED DESCRIPTION

Figure 1:
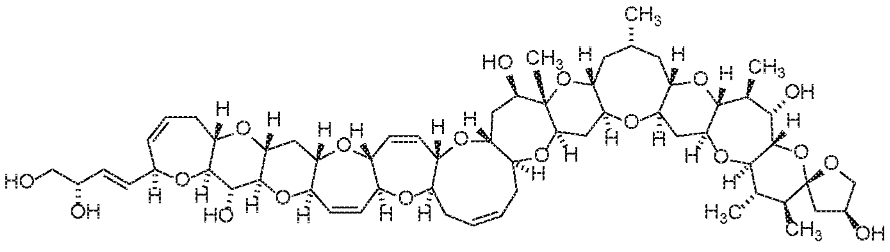
FIG. 1 shows the chemical structure of one form of ciguatoxin.

This disclosure includes chemical structures that show atomic compositions of compounds and relative bonding arrangements of atoms in a chemical compound. Unless specifically stated, the geometric arrangement of atoms shown in the chemical structures is not intended to be an exact depiction of the geometric arrangement of every embodiment, and those skilled in the chemical arts will recognize that compounds may be similar to, or the same as, the illustrated compounds while having different molecular shapes or conformations. For example, the structures denoted herein may show bonds extending in one direction, while embodiments of the same compound may have the same bond extending in a different direction. Additionally, bond lengths and angles, Van der Waals interactions, isoelectronic structures, and the like may vary among instances of the same chemical compound. Additionally, unless otherwise noted, the disclosed structures cover all stereoisomers, conformers, rotamers, isomers, and enantiomers of the represented compounds.

Numbered chemical structures are numbered using numbers, or numbers and letters, in parentheses. Unless otherwise noted, chemical reactions are performed at ambient conditions or under slight heating with no special atmosphere or head space, and may be performed using standard organic solvents to manage mix properties such as viscosity and flow index. Standard procedures for quenching the reaction, solvent removal, and purification are performed.

The following abbreviations may be used herein: THF (also referred to as thf) is tetrahydrofuran, DCM (also referred to as dcm) is dichloromethane, tol is toluene, and EtOAc is ethyl acetate.

As used herein, the term "substituted" means that a hydrogen group has been replaced with a heteroatom, or a heteroatom-containing group. For example, a "substituted hydrocarbyl" is a radical made of carbon and hydrogen where at least one hydrogen is replaced by a heteroatom or heteroatom-containing group.

The terms "alkyl group," "alkyl radical," "alkyl," "hydrocarbyl radical," "hydrocarbyl," and "hydrocarbyl group" are used interchangeably throughout this document. Likewise, the terms "group," "radical," and "substituent" are also used interchangeably in this document. For purposes of this disclosure, "alkyl group" refers to $C_1$-$C_{100}$ radicals, that may be linear, branched, or cyclic, and when cyclic, aromatic or non-aromatic. Examples of such radicals include methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and their substituted analogues. Substituted alkyl radicals are those in which at least one hydrogen atom of the hydrocarbyl radical has been substituted with at least one halogen (such as Br, Cl, F or I) or at least one functional group such as C(O)R*, C(O)NR*$_2$, C(O)OR*, NR*$_2$, OR*, SeR*, TeR*, PR*$_2$, AsR*$_2$, SbR*$_2$, SR*, BR*$_2$, SiR*$_3$, GeR*$_3$, SnR*$_3$, and PbR*$_3$ (where R* is independently a hydrogen or hydrocarbyl radical, and two or more R* may join together to form a substituted or unsubstituted saturated, partially unsaturated or aromatic cyclic or polycyclic ring structure), or where at least one heteroatom has been inserted within a hydrocarbyl ring.

The term "aryl" or "aryl group" includes a $C_4$-$C_{20}$ aromatic ring, such as a six carbon aromatic ring, and the substituted variants thereof, including phenyl, 2-methylphenyl, xylyl, 4-bromo-xylyl, etc. Likewise, heteroaryl means an aryl group where a ring carbon atom (or two or three ring carbon atoms) has been replaced with a heteroatom, preferably N, O, or S. As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

Where isomers of a named alkyl or aryl group exist (e.g., n-butyl, iso-butyl, sec-butyl, and tert-butyl) reference to one member of the group (e.g., n-butyl) shall expressly disclose the remaining isomers (e.g., iso-butyl, sec-butyl, and tert-butyl) in the family. Likewise, reference to an alkyl or aryl group without specifying a particular isomer (e.g., butyl) expressly discloses all isomers (e.g., n-butyl, iso-butyl, sec-butyl, and tert-butyl).

For any particular compound disclosed herein, any general or specific structure presented also encompasses all conformational isomers, regioisomers, and stereoisomers that may arise from a particular set of substituents, unless stated otherwise. Similarly, unless stated otherwise, the general or specific structure also encompasses all enantiomers, diastereomers, and other optical isomers whether in enantiomeric or racemic forms, as well as mixtures of stereoisomers, as would be recognized by a skilled artisan. In some embodiments, the compounds described herein can contain one or more chiral centers. These can include racemic mixtures, diastereomers, enantiomers, and mixtures containing one or more stereoisomer. Further, the disclosed compounds can encompass racemic forms of the compounds in addition to individual stereoisomers, as well as mixtures containing any of these.

The word "compound," as used herein, includes any chemical structure in which two or more chemical elements are bonded together. Thus, "compound" includes, but is not limited to, small molecules, cross-linkers, monofunctional molecules, monomers, and polymers.

In some embodiments, toxins are the target substance to be detected. Such toxins include ciguatoxins, which comprise a suite of polyketides, which are part of a larger family of dinoflagellate-derived polyketide toxins that pose a threat to human health. Ciguatoxins include several side chain variants. FIG. 1 shows the chemical structure of one form of ciguatoxin, CTX-1, specifically, CTX-1B. Other forms of ciguatoxin (CTX) include CTX-2, CTX-3, gambiertoxin (CTX-4B), and scaritoxin. Examples of other toxins of interest include brevetoxin, okadaic acid, and the related kinophysistoxins, pectenotoxins, yessotoxin, and the azaspiracids.

Ciguatoxins do not possess a useful chromophore for selective spectroscopic detection but contain a relatively reactive primary hydroxyl group through which a label could be attached prior to detection. Unfortunately, after attachment of the label, a more extensive analytical technique is required for detection. Such techniques are likely unavailable outside of accredited testing laboratories.

Some of the methods herein use a turbidimetric assay as a fast detection method for ciguatoxin in seafood extract, without the use of a chromophore. Polymerization of a functionalized target substance (such as an acrylate-bound ciguatoxin) results in the precipitation of the complex which is accompanied by a turbidimetric response. That is, as the complex precipitates from solution, the solution becomes 'cloudy' and the turbidity can be correlated to concentration. In another embodiment and as discussed below, the method for detecting ciguatoxin uses a chromophore (e.g., polythiophenes).

Detecting Target Substances by Turbidimetric Analysis

Figure 2:
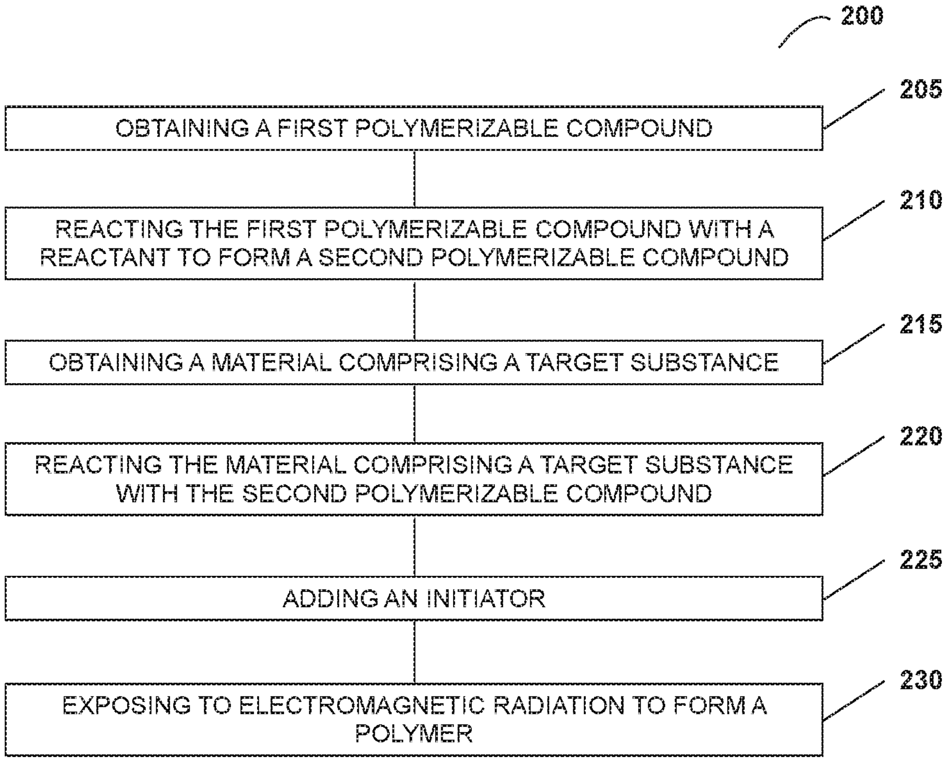
FIG. 2 illustrates a method of forming a polymer according to some embodiments.
Figure 3:
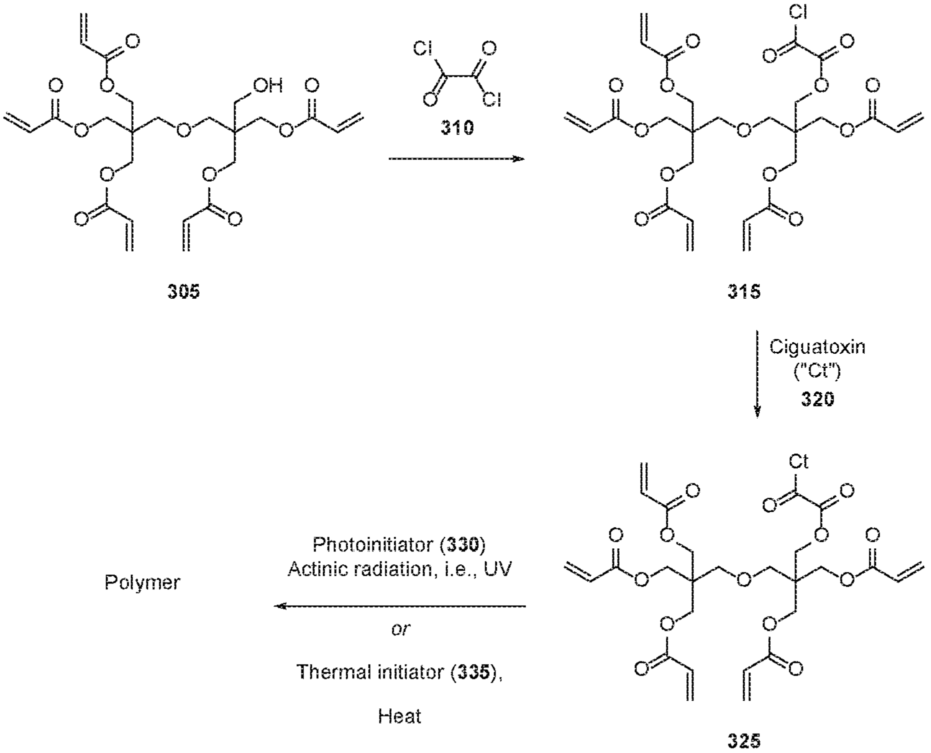
FIG. 3 shows a chemical reaction diagram illustrating a method of forming a polymer according to some embodiments.

FIGS. 2 and 3 illustrate a method of solidifying compositions including a target substance (e.g., via crosslinking and/or polymerizing) according to some embodiments. The target substance is the substance to be detected. In some embodiments the target substance includes ciguatoxin. Two broad classes of solidifiable compositions are compositions that become solid through a process of polymerization, and compositions that become solid by cross-linking. However, for the purposes of the present disclosure, it will be appreciated that the mechanism by which the material is solidified is not critical, so long as identification of the target substance can be accomplished.

For purposes herein, crosslinking is a form of polymerization and the term "polymerization" includes "crosslinking." The term "polymerizable" includes the term "crosslinkable".

Typically, polymerization is characterized by the joining of simple monomers to each other, or to pre-existing oligomers or polymers, to form a high molecular weight molecule, such as a polymer. The polymer may be linear or branched, and may be made from identical monomers, or from two or more different monomers (whereupon a "copolymer" is formed). In contrast, crosslinking occurs between light-sensitive and/or thermally-sensitive monomers and/or polymers (monomers and/or polymers possessing in their chain a polymerizable functional groups), or between polymers in the presence of a polymerizable crosslinker. The speed of polymerization and/or crosslinking in the methods and systems described herein is controlled by a photoinitiator (or a thermal initiator), typically an agent that forms free radicals when illuminated by light of appropriate wavelengths (or when heated).

With reference now to FIGS. 2 and 3, the method of forming a detectable composition includes obtaining a first polymerizable compound at operation 205. An example of polymerizable compound includes crosslinkable compounds, including dipentaerythritol pentaacrylate 305 available from Alfa Chemistry. Although an acrylate is described, it is contemplated that any compound capable of chemically bonding to the target substance and capable of crosslinking and/or polymerizing is suitable. Such compounds include acrylate, methacrylate, acrylamide, methacrylamide, vinyl acetate, vinyl formamide, epoxide, aldehyde, halohydrins, disulfonate esters, esters, acid halides, carboxylic acids, carboxylic acid anhydrides, melamine resins, hydroxymethyl ureas, isocyanates, thioethers, derivatives thereof, or combinations thereof (e.g., 3-(acryloyloxy)-2-hydroxypropyl methacrylate; pentaerythritol diacrylate monostearate; and pentaerythritol triacrylate). The type of crosslinking and/or polymerization can depend on the polymerizable and/or crosslinking functional group. For example, if the target substance is bound to a compound having an epoxide functionality, the epoxides can crosslink and/or polymerize under cationic polymerization.

Method 200 includes reacting the first polymerizable compound (e.g., a multifunctional acrylate) with a reactant at operation 210 for an empirically determined time at an empirically determined temperature to form a second polymerizable compound. Such reactions are reactions known to those skilled in the art such as nucleophilic acyl substitution, esterification, etc. The temperature and time depends on various factors such as the reactivity of the first compound and the reactant. The reactant can include any reactant that transforms the first polymerizable compound to the second polymerizable compound, and the second polymerizable compound should be more reactive to functionality of the target substance. For example, the reactant can be an acid halide such as (e.g., oxalyl chloride 310). Other reactants can be oxalyl bromide, malonyl chloride, malonyl bromide, succinyl chloride, succinyl bromide, glutaryl chloride, glutaryl bromide, adipyl chloride, adipyl bromide, and similar compounds with two terminal acid chlorides and/or acid bromides. In this example, alcohol 305 is transformed to a more reactive chloride 315 using acid halide 310. In some embodiments, operation 210 can be skipped when the first polymerizable compound can react with the target substance.

In an embodiment, chloride 315 may be synthesized according to the following procedure. To a solution of dipentaerythritol pentaacrylate (10 mmol) in $CH_2Cl_2$ (dichloromethane) was added oxalyl chloride (15 mmol) and 1 drop of dimethylformamide (DMF) as a catalyst. The mixture was allowed to stir at room temperature (e.g., about 15° C. to about 25° C.) for about 5 hours. The volatiles are removed under reduced pressure. Standard procedures for purification are then completed to give chloride 315.

Method 200 includes obtaining a material comprising a target substance at operation 215. In some embodiments, the target substance is ciguatoxin. It is contemplated that other toxins and target substances (and their metabolites) bearing a primary hydroxyl group can be detected. It is also contemplated that other biotoxins, chemical compounds, or other contaminants indicative of aquatic stress can be identified. The material comprising the toxic substance includes any material containing a toxin, such as seafood, fish, aquatic invertebrates, tissue samples, samples that are macerated and extracted in a suitable solvent, water samples, plant samples, and other aquatic samples.

Method 200 includes reacting the material comprising the target substance with the second polymerizable compound to form a functionalized target substance at operation 220. For example, the target substance is ciguatoxin ("Ct") 320 and the second polymerizable compound is chloride 315. In this example, the primary hydroxyl of ciguatoxin reacts with the chloride of the second polymerizable compound to form a functionalized ciguatoxin 325 (or other substance to be detected).

Method 200 includes adding an initiator (330 and/or 335) to promote polymerization and/or crosslinking at operation 225. Suitable initiators include photoinitiators such as (2,4,6-trimethylbenzoyl)diphenylphosphine oxide (TMDPO). Photoinduced reactions can be run at temperatures of about room temperature (about 15° C. to about 25° C.). Suitable thermal initiators include AIBN and benzopinacol at about 60° C. to about 80° C. The polymerization and/or crosslinking may be performed with or without solvent. The Suitable solvents for the polymerization and/or crosslinking include $CH_2Cl_2$, $CCl_4$, and benzene.

Other photoinitiators that may be used include 2,2-dimethoxy-2-phenyl acetophenone (DMPA), benzophenone, thioxanthone, and camphorquinone. Other photoinitiators include other acetophenones, benzil and benzoin compounds, benzophenones, cationic photoinitiators, and thioxanthones.

Other suitable thermal initiators that may be used include tert-amyl peroxybenzoate; 1,1'-azobis(cyclohexanecarbonitrile); 2,2'-azobisisobutyronitrile (AIBN); 2,2-bis(tert-butylperoxy)butane; 1,1-bis(tert-butylperoxy)cyclohexane; 2,5-bis(tert-butylperoxy)-2,5-dimethylhexane; 2,5-bis(tert-butylperoxy)-2,5-dimethyl-3-hexyne; bis(1-(tert-butylperoxy)-1-methylethyl)benzene; 1,1-Bis(tert-butylperoxy)-3,3,5-(dibutyl phthalate)trimethylcyclohexane; tert-butyl hydroperoxide; tert-butyl peracetate; tert-butyl peroxide; tert-butyl peroxybenzoate; tert-butylperoxy isopropyl carbonate; cumene hydroperoxide; cyclohexanone peroxide, dicumyl peroxide, lauroyl peroxide; peracetic acid.

Suitable cationic photoinitiators that may be used include bis(4-tert-butylphenyl)iodonium perfluoro-1-butanesulfonate; bis(4-tert-butylphenyl)iodonium p-toluenesulfonate; bis(4-tert-butylphenyl)iodonium triflate; boc-methoxyphenyldiphenyl sulfonium triflate; (4-tert-butylphenyl)diphenylsulfonium triflate; diphenyliodonium hexafluorophosphate; diphenyliodonium nitrate; diphenyliodonium perfluoro-1-butanesulfonate; diphenyliodonium p-toluenesulfonate; diphenyliodonium triflate; (4-fluorophenyl)diphenylsulfonium triflate; N-hydroxynaphthalimide triflate; N-hydroxy-5-norbornene-2,3-dicarboximide perfluoro-1-butanesulfonate; (4-iodophenyl)diphenyl sulfonium triflate; (4-methoxyphenyl)diphenyl sulfonium triflate; 2-(4-methoxystyryl)-4,6-bis(trichloromethyl)-1,3,5-triazine; (4-methylphenyl)diphenyl sulfonium triflate; (4-methylthiophenyl)methyl phenyl sulfonium triflate; 1-naphthyl diphenylsulfonium triflate; (4-phenoxyphenyl) diphenyl sulfonium triflate; (4-phenylthiophenyl)diphenyl sulfonium triflate; triaryl sulfonium hexafluoroantimonate salts; triaryl sulfonium hexafluorophosphate salts; triphenyl sulfonium perfluoro-1-butanesulfonate; triphenyl sulfonium triflate; tris(4-tert-butylphenyl)sulfonium perfluoro-1-butanesulfonate; and tris(4-tert-butylphenyl)sulfonium triflate. Additionally, aryl onium salts known to those of skill in the art are suitable as cationic photoinitiators.

The amount of initiator is empirically determined based on factors such as reaction time. Typically, the amount of initiator is between about 0.01 and about 12 mol %, preferably between about 0.1 and about 10 mol %, more preferably between about 1 and about 5 mol %.

Method 200 includes exposing the mixture to electromagnetic radiation. Such radiation may include actinic radiation, i.e., electromagnetic radiation that can produce photochemical reactions, including UV light and visible light, including wavelengths of about 200 nm to about 500 nm. Alternately, method 200 includes exposing the mixture to thermal radiation. Temperatures for the reaction can be empirically determined, with the choice of polymerization initiator depending on factors such as solubility and decomposition temperature (i.e., high temperature providing better solubility for the reactants, but an increased risk of decomposition). Upon exposure to the electromagnetic radiation, the polymerizable and/or crosslinking groups (such as the acrylates of 325) polymerize and/or crosslink.

If the polymerization is performed in an organic solvent, then the initiator should be soluble in that solvent and the decomposition temperature of the initiator must be at or below the boiling point of the solvent. Initiators such as 2,2'-Azobis(2-methylpropionitrile) and benzoyl peroxide suit these requirements. If the desired polymerization occurs at or below 20° C., then low temperature free radical initiators can be used. Various Azo-type initiators can be chosen for range of decomposition temperatures.

It should be noted that one or more of the operations may occur before or after that shown in FIG. 2 or may occur simultaneously in some embodiments. For example, operations 205 and 210 may occur after operation 215.

Figure 4:
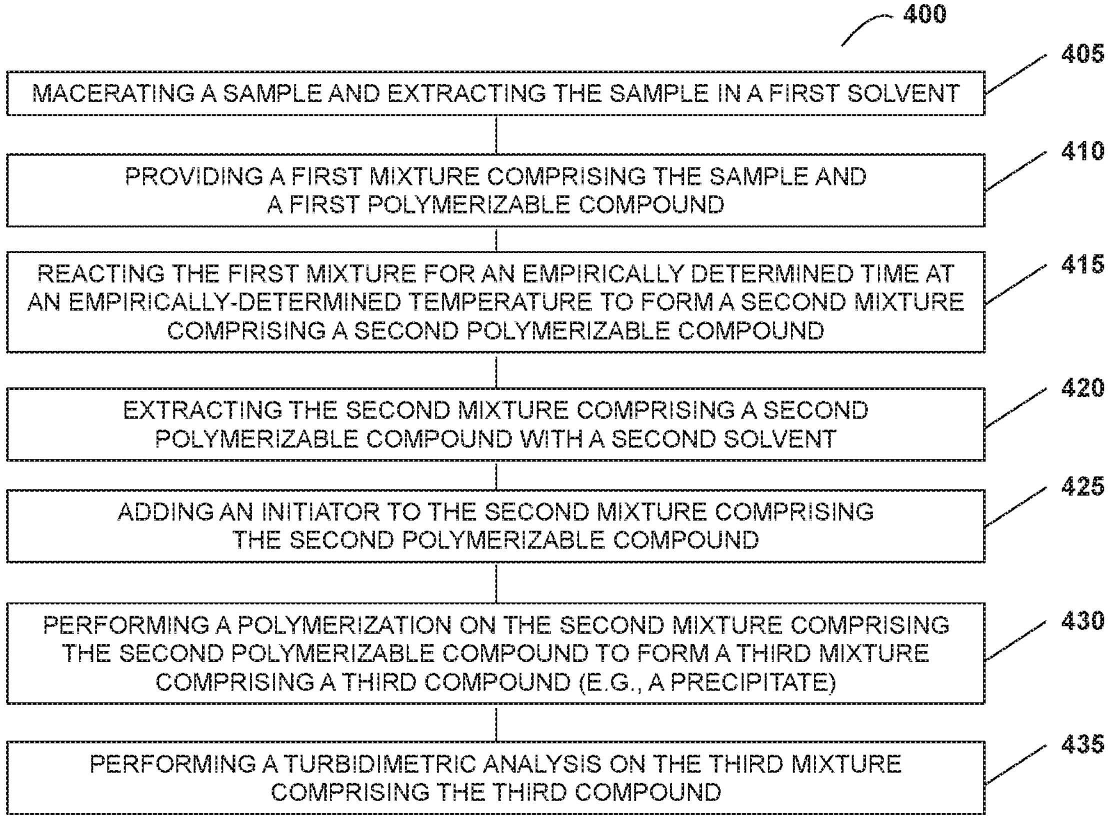
FIG. 4 illustrates a method of detecting a target substance according to some embodiments.

FIG. 4 illustrates a method 400 for detecting a target substance, for example ciguatoxin, according to some embodiments. It is contemplated that other toxins and target substances (and their metabolites) bearing a primary hydroxyl group can be detected. It is also contemplated that other biotoxins, chemical compounds, or other contaminants indicative of aquatic stress can be identified.

At operation 405, a sample is macerated and extracted in a suitable first solvent in which the target substance is soluble. This first solvent is an oil that is liquid at about room temperature (between about 15° C. and about 25° C.). Examples of the first solvent include liquid triglycerides (such as vegetable oil, olive oil, linseed oil, flax seed oil, and combinations thereof) and fatty acids that are liquids at room temperature. Alternately, the first solvent may be a nonpolar solvent such as heptane, naptha, xylene, toluene, $CH_2Cl_2$, or combinations thereof. This operation may involve mechanical stirring, sonic agitation, chemical extraction, etc. The extract may additionally be filtered. The sample includes any material containing a toxin, such as seafood, fish, aquatic invertebrates, tissue samples, samples that are macerated and extracted in a suitable solvent, water samples, plant samples, and other aquatic samples.

To the extract is added an empirically determined quantity of first polymerizable compound to form a first mixture at operation 410. In some embodiments, the amount of first polymerizable compound added is greater than about 1 equivalent relative to the target substance. It should be noted that an initiator may also be added during this operation. The first compound is a multifunctional compound having polymerizable and/or crosslinkable groups (e.g., a multifunctional acrylate bearing chloride). The multifunctional compound can be any compound capable of chemically bonding to the target substance and capable of crosslinking and/or polymerizing. Regarding bonding to the target substance, the first polymerizable compound should bear a substituent that reacts with, for example, ciguatoxin's primary hydroxyl. Regarding crosslinking and/or polymerizing, the such compounds include acrylate, methacrylate, acrylamide, methacrylamide, vinyl acetate, vinyl formamide, epoxide, aldehyde, halohydrins, disulfonate esters, esters, acid halides, carboxylic acids, carboxylic acid anhydrides, melamine resins, hydroxymethyl ureas, isocyanates, thioethers, derivatives thereof, or combinations thereof (e.g., dipentaerythritol pentaacrylate; 3-(acryloyloxy)-2-hydroxypropyl methacrylate; pentaerythritol diacrylate monostearate; and pentaerythritol triacrylate).

The first mixture is allowed to react for an empirically determined time at an empirically determined temperature to form a second mixture comprising a second polymerizable compound at operation 415. As described above, the temperature and time will depend on the reactivity of the first polymerizable compound. In an embodiment and as described above, chloride 315 is the first polymerizable compound. The first polymerizable compound reacts with the target substance (e.g., ciguatoxin) in the extract under ambient conditions.

In some embodiments, a method of removing the unreacted materials (i.e., first compound) depends on the precise characteristics of the materials. Extracting with a solvent to remove unreacted materials is one such removal method. Another method may include chromatography.

At operation 420, which is optional, the second mixture comprising the second polymerizable compound is subjected to an extraction with a second solvent and the second mixture comprising the second polymerizable compound is retained. The second solvent may be any suitable solvent, with alcohols such as methanol, ethanol, and isopropanol most often preferred. The second mixture comprising the second polymerizable compound may be an oil phase. This operation removes the unreacted first polymerizable compound (e.g., acrylate) from the phase comprising the second polymerizable compound. The extraction solvent should be selected such that the first polymerizable compound and the second polymerizable compound can be separated.

It will be apparent that the extraction solvent for first polymerizable compound should not also be an efficient solvent for the second polymerizable compound.

At operation 425, an initiator (e.g., photoinitiator, thermal initiator) is added to the second mixture comprising the second polymerizable compound. The initiator can be any initiator, including any initiator described herein. The amount of initiator added is empirically determined, typically between about 0.01 mol % and about 12 mol %, preferably between about 0.1 mol % and about 10 mol %, more preferably between about 1 mol % and about 5 mol %. At operation 430, the second mixture comprising the second polymerizable compound is polymerized to form a third mixture comprising a third compound. The third compound represents the crosslinked and/or polymerized product comprising the target substance to be detected. The third compound may be in the form of a solid such as a precipitate, particles, and aggregates. The polymerization can include exposing the second mixture to electromagnetic radiation (e.g., UV, heat) for an empirically determined amount of time and an empirically determined temperature to form a third mixture comprising a third compound. The amount of time needed for the reaction can depend on a number of factors such as the type of initiator and the type of cross-linkable and/or polymerizable functional groups (e.g., acrylates, formamides, epoxides) of the second polymerizable compound.

For ultraviolet (UV)-based polymerization, the polymerization may also depend on the intensity of light and the temperature of the reaction mixture. For thermal-based polymerization, the polymerization may also depend on the heat of the reaction mixture.

In an embodiment, a radiant energy source such as an ultraviolet curing lamp can be applied to the reaction mixture for a predetermined amount of time. The source of UV light can include UV lamps such as those used for cosmetic nail care and dental procedures. It will be appreciated that visible light may also be used to cure the composition. Applying UV radiation (about 10 nm to about 400 nm) to the composition activates the photoinitiator and promotes crosslinking of the reactive functional groups.

Suitable sources of illumination are any source that emits radiation from about 10 nm to about 700 nm. The preferred wavelength of the illumination will depend on the particular photoinitiator or crosslinking/polymerizable functional group used. Suitable illuminating sources include mercury arcs, carbon arcs, tungsten filament lamps, xenon arcs, krypton arcs, sunlamps, lasers, and the like, with mercury arcs, e.g., a 100 W mercury arc lamp, most preferred. Often, multichromatic light will result in most efficient photopolymerization. The use of multichromatic light for photopolymerization is well understood by those of skill in the art. However, monochromatic light, e.g., laser light, is also useful. In some embodiments, it is desirable to place an infrared filter between the light source and the target to avoid the generation of large amounts of heat.

In a preferred embodiment, the source and intensity of illumination will be chosen or adjusted so that sufficient polymerization or crosslinking occurs within about 0.5 minutes to about 10 minutes exposure time, preferably about 2 minutes exposure time. The amount of time required for solidification (e.g., polymerization and/or crosslinking) will depend on a number of factors including the type of lamp used, and the wavelengths emitted (or when light filters are used, the wavelengths of the radiation striking the solidifiable material).

At operation 435, a turbidimetric analysis is performed on the oil phase comprising the third compound (e.g., precipitate) and the result correlated to a target substance concentration via a calibration curve prepared independent of the sample. The calibration curve measures scattered light intensity as a function of concentration. Turbidity can be measured in multiple ways, for example, by a nephelometer. The amount of light scattered is influenced by many aspects of the particles like color, shape, and reflectivity. Because of this, and the fact that heavier particles may settle quickly and may not contribute to the turbidity reading, the relationship between turbidity and total suspended solids (TSS) can change depending on test sample preparation.

Kits for the Turbidimetric Analysis

The disclosure also includes systems for carrying out the methods described herein according to some embodiments. Typically, a system to be used for turbidimetric analysis includes a multifunctional monomer, an initiator, one or more solvents and one or more extraction solvents. The initiator can be a photoinitiator, a thermal initiator, or a combination thereof. Examples of initiators are described above. The solvent(s) and extraction solvent(s) may be any solvent and extraction liquid described above.

The multifunctional monomer is a compound having polymerizable and/or crosslinkable functionality including compounds comprising an acrylate, methacrylate, acrylamide, methacrylamide, vinyl acetate, vinyl formamide, epoxide, aldehyde, halohydrins, disulfonate esters, esters, acid halides, carboxylic acids, carboxylic acid anhydrides, melamine resins, hydroxymethyl ureas, isocyanates, thioethers, derivatives thereof, or combinations thereof (e.g., 3-(acryloyloxy)-2-hydroxypropyl methacrylate; pentaerythritol diacrylate monostearate; and pentaerythritol triacrylate). In some embodiments, the polymerizable monomer is a derivative of dipentaerythritol pentaacrylate. The multifunctional monomer reacts with the target substance.

In some embodiments, the system further comprises one or more of a container, a light source, and a heat source. The light source may be one or more of those described herein. The heat source may include any suitable heating apparatus including a hot lamp and a heating mantle.

Detecting Target Substances by Colorimetric Analysis

As discussed earlier, a rapid detection method for ciguatoxin in food is desirable. As an alternate to the aforementioned method and compositions using turbidimetric analysis to detect ciguatoxin, the detection method can use a colorimetric assay. A polythiophene imparts the color change to the ciguatoxin. In an embodiment, a polythiophene, either in solution or as part of a gel/solid detection matrix, possessing acyl chloride-functionalized side chains will bind to the reactive primary hydroxyl group of the ciguatoxin.

Polythiophene, specifically polythiophene functionalized at the 3-position with an alkyl chain, is a well-known conjugated polymer with a planar backbone that results in a "low band-gap" that makes polythiophene purple in the solid state and red-purple in solution. Disruption of the planar, conjugated backbone results in a blue shift in absorbance that can be seen by the unaided eye, and also by UV-Vis spectrometry in cases of less obvious spectral shifts or color blindness.

Figure 5:
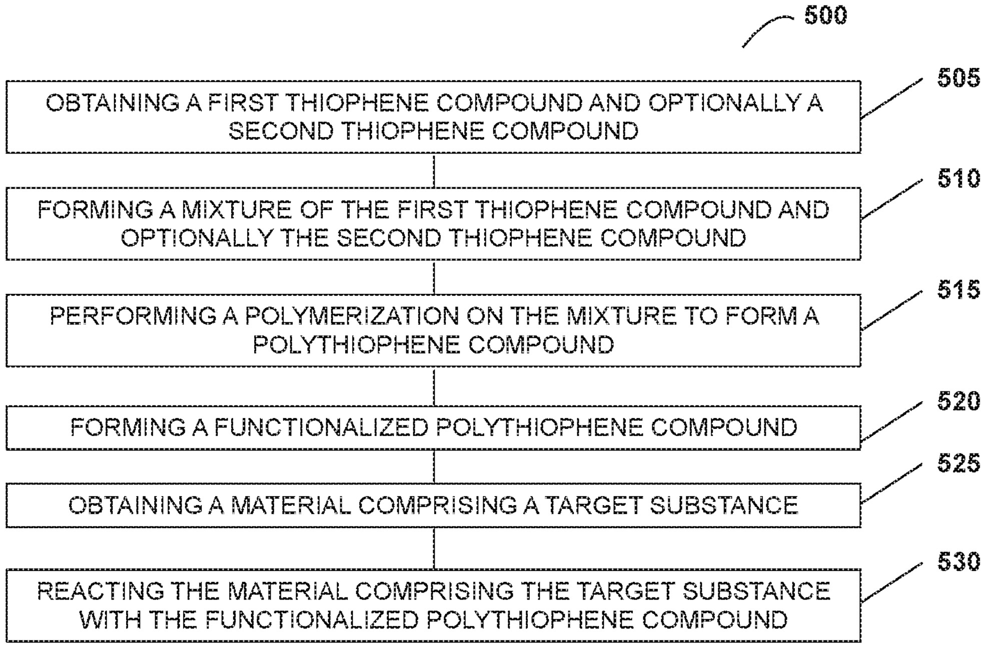
FIG. 5 illustrates a method of forming a polymer according to some embodiments.
Figure 6:
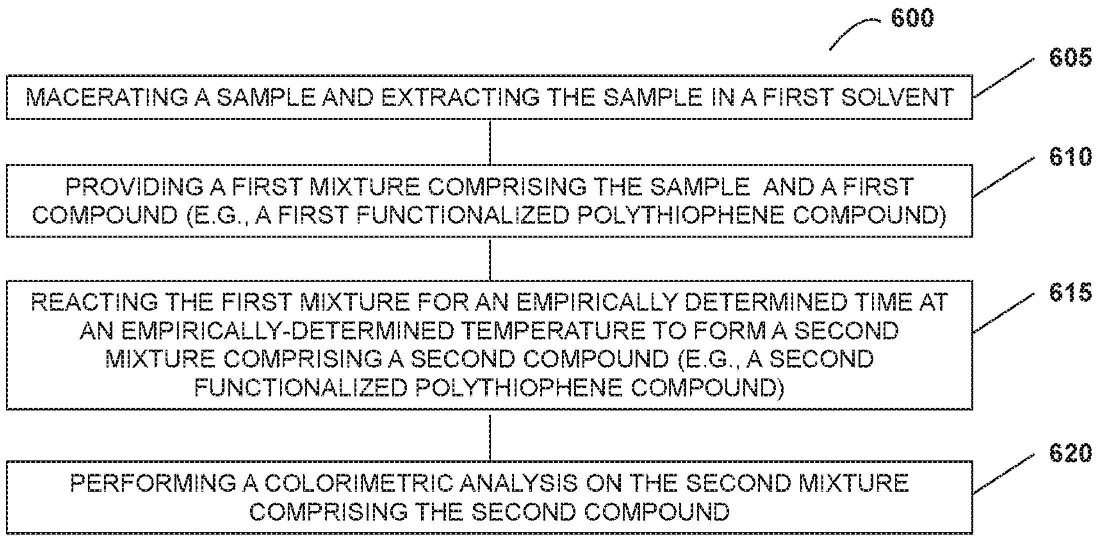
FIG. 6 illustrates a method of detecting a target substance according to some embodiments.
Figure 7:
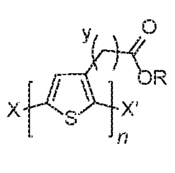
FIG. 7 shows various polythiophene chromophores according to some embodiments.
Figure 7:
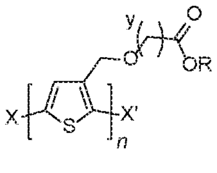
Figure 7:
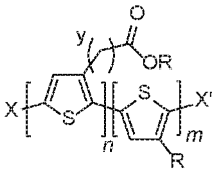
Figure 7:
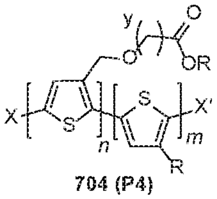
Figure 7:
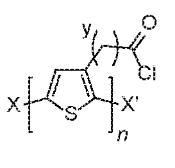
Figure 7:
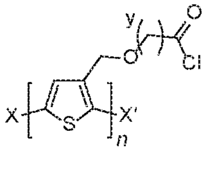
Figure 7:
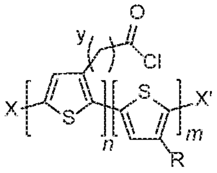
Figure 7:
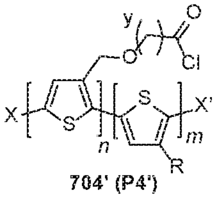

FIGS. 5 and 6 illustrate a method of detecting compositions including a target substance according to some embodiments. The target substance is the substance to be detected. In some embodiments, the target substance is ciguatoxin. It is contemplated that other toxins and target substances (and their metabolites) bearing a primary hydroxyl group can be detected. It is also contemplated that other biotoxins, chemical compounds, or other contaminants indicative of aquatic stress can be identified. FIGS. 7-9, 10A, and 10B illustrate methods for synthesizing polythiophene chromophores, for example 701 (P1), 702 (P2), 703 (P3), and 704 (P4), according to some embodiments. In some embodiments, each R is independently alkyl or substituted alkyl, each X and X' is independently hydrogen or bromine y is an integer between 1 and 17, m is an integer between 8 and 1200, and n is an integer between 8 and 1200. The polythiophene chromophores can be functionalized as an acyl chloride and can react with the primary hydroxyl group of the ciguatoxin molecule. Examples of the acyl chlorides are 701' (P1'), 702' (P2'), 703' (P3'), and 704' (P4'), wherein each R is independently alkyl or substituted alkyl, each X and X' is independently hydrogen or bromine, y is an integer between 1 and 17, m is an integer between 8 and 1200, and n is an integer between 8 and 1200.

It is contemplated that any chromophoric polythiophene compound may be used. Exemplary polythiophene compounds include homopolymers 701 (P1), 702 (P2), 701' (P1'), and 702' (P2'), and copolymers 703 (P3), 704 (P4), 703' (P3'), and 704' (P4'). These copolymers may be random patterned copolymers or block copolymers. While alkyl groups with a single carbon spacer group (y=1) are illustrated here, alkyl chains of varying lengths (e.g., y=1-17; one to eleven carbon spacer groups) can be used. The carbon chain length (y=1-17) between the thiophene ring and the ester can be altered so as to tune the properties of the final polymer with respect to the planarity both before and after reacting with ciguatoxin.

Figure 8:
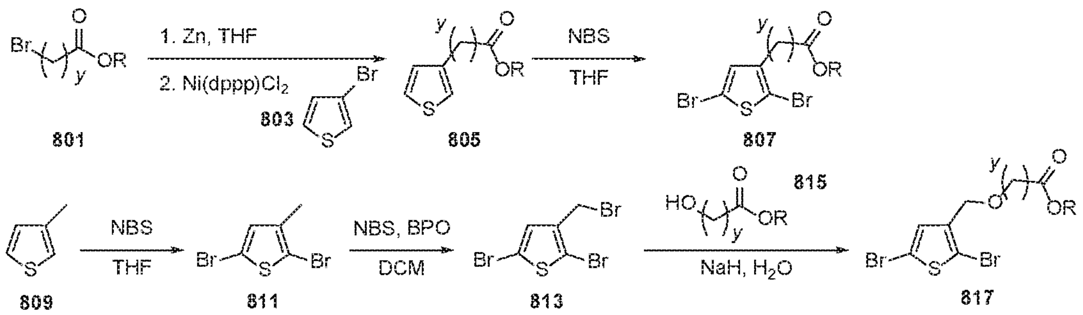
FIG. 8 shows the synthesis of exemplary ester-functionalized thiophene monomers according to some embodiments.

With reference now to FIG. 5, the method 500 of forming a detectable composition includes obtaining a first thiophene compound and optionally a second thiophene compound at operation 505. In some embodiments, the first and second thiophene compounds are ester-terminated dibromoalkylthiophenes. FIG. 8 details the synthesis of two different ester-terminated dibromoalkylthiophene monomers 807 and 817 according to some embodiments.

In an embodiment and as shown in FIG. 8, terminal bromo-alkanoic acid ethyl ester compound 801 (y=1-17) may be reacted with 3-bromothiophene 803 via a Negishi coupling according to the following procedure. Terminal bromo-alkanoic acid ethyl ester (89 mmol) is added to a tetrahydrofuran (THF) suspension of activated zinc (Zn) and stirred for about 2 hours at about room temperature under argon. The zinc particles are allowed to settle and the supernatant organozinc compound is added dropwise to a solution 3-bromothiophene (16.81 g, 103 mmol) and [1,3-Bis(diphenylphosphino)propane]dichloronickel(II) (Ni(dppp)$Cl_2$, 5 mol %) in THF. The reaction is stirred for about 48 hours at about room temperature and quenched with a saturated $NH_4Cl$ solution. After extraction with diethyl ether (3×200 ml), the organic phase is dried over $MgSO_4$, filtered, and the solvents are removed in vacuo. The resulting crude product is purified by standard procedures for purification, for example, distillation. Standard procedures for isolation and purification (for example, vacuum distillation) are then performed to provide ester 805 (y=1-17).

In an embodiment, dibromination of ester 805 (y=1-17) using N-bromosuccinimide (NBS) to provide dibromoalkylthiophene monomer 807 may be accomplished according to the following procedure. To a stirring solution of a 3-alkylester-thiophene 805 (94 mmol) in 250 mL of either tetrahydrofuran, chloroform, glacial acetic acid, or a mixture of these three solvents is added N-bromosuccinimide (NBS, 200 mmol) portion-wise. The reaction mixture is stirred for about 5 hours and diluted with $H_2O$ (300 ml). The organic layer is extracted with hexane or diethyl ether (3 times). The combined organic layers are washed with 1N NaOH, then washed with $H_2O$, and then washed with brine, and then dried over $MgSO_4$. The solvents are removed in vacuo. Standard procedures for isolation and purification (for example, vacuum distillation) are then performed to provide ester-terminated dibromoalkylthiophene monomers 807 (y=1-17).

In an embodiment and as shown in FIG. 8, ether-linked ester terminated dibromoalkylthiophene monomer 817 may be synthesized by consecutive brominations using NBS, followed by a nucleophilic reaction of terminal hydroxyl ester 815 (y=1-17) with tribromoalkylthiophene 813. A dibromination operation may be performed according to the following procedure. To a stirring solution of methylthiophene 809 (94 mmol) in 250 mL of either tetrahydrofuran, chloroform, glacial acetic acid, or a mixture of these three solvents is added N-bromosuccinimide (NBS, 200 mmol) portion-wise. The reaction mixture is stirred for about 5 hours and diluted with $H_2O$ (300 ml). The organic layer is extracted with hexane or diethyl ether (three times). The combined organic layers are washed with 1N NaOH, then washed with $H_2O$, then washed with brine, and then dried over $MgSO_4$. The solvents are removed in vacuo. Standard procedures for isolation and purification (for example, vacuum distillation) are then performed to provide 2,5-dibromo-3-methylthiophene 811.

In an embodiment and as shown in FIG. 8, tribromoalkylthiophene 813 may be synthesized according to the following procedure. To a stirring, refluxing solution of 2,5-dibromo-3-methylthiophene 811 (10 mmol) in 50 ml of anhydrous dichloromethane or anhydrous benzene is added NBS (52.5 mmol) and benzoyl peroxide (BPO, 0.5 mol %) portion-wise via a powder addition funnel. The reaction mixture is stirred for about 3 hours and diluted with $H_2O$ (200 ml). The organic layer is extracted with diethyl ether (three times). The combined organic layers are washed with $H_2O$ and brine, and then dried over $MgSO_4$. The solvents are removed in vacuo. Standard procedures for isolation and purification (for example, vacuum distillation) are then performed to provide tribromoalkylthiophene 813.

In an embodiment and as shown in FIG. 8, ester-terminated dibromoalkylthiophene monomer 817 may be synthesized according to the following procedure. To a stirring solution of sodium hydride (NaOH, 1.1 equiv) in anhydrous THF (200 ml) is added a solution of terminal hydroxylester 815 (y=1-17, 50 mmol) in THF (25 ml) at about 0° C. under an argon atmosphere. The reaction is stirred for about 4 hours at about room temperature and then quenched with water. The organic layer is extracted with diethyl ether (three times). The combined organic layers are washed with $H_2O$ and brine, and then dried over $MgSO_4$. The solvents are removed in vacuo. Standard procedures for isolation and purification (for example, vacuum distillation) are then performed to provide ester-terminated dibromoalkylthiophene monomer 817 (y=1-17).

Figure 9A:
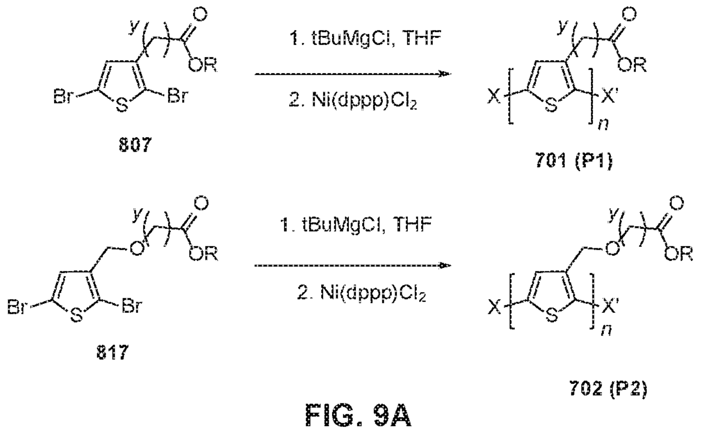
FIG. 9A shows the synthesis of exemplary polythiophene homopolymers according to some embodiments.
Figure 9B:
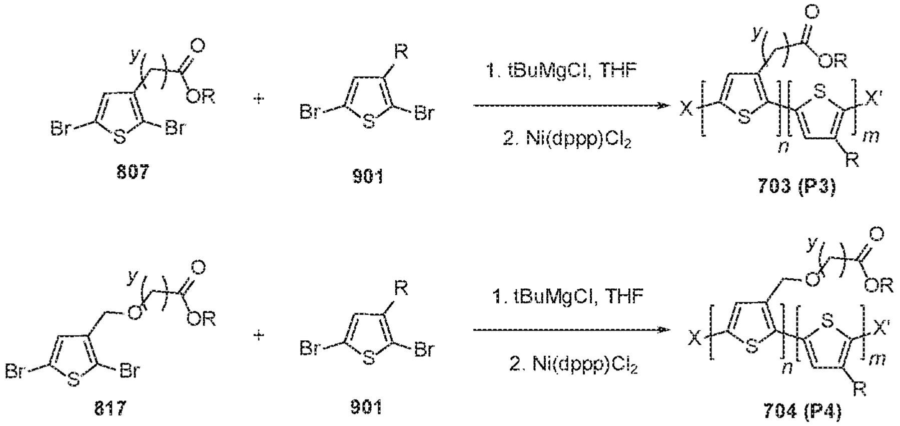
FIG. 9B shows the synthesis of exemplary polythiophene copolymers according to some embodiments.

The method 500 of forming a detectable composition includes forming a mixture of the first thiophene compound and optionally a second thiophene compound at operation 510. At operation 515, a polymerization reaction is performed on the mixture to form a polythiophene compound. If the mixture has one thiophene, a homopolymer (for example, polythiophenes 701 (P1) and 702 (P2)) is formed (FIG. 9A). If the mixture has more than one thiophene (i.e., a first thiophene compound and a second thiophene compound), a copolymer (for example, polythiophenes 703 (P3) and 704 (P4)) is formed (FIG. 9B). The copolymers allow tuning of the ester content in the polymer, and thus allowing for control of the acid chloride content in the functionalized polythiophene.

In an embodiment, the polymerizations are performed via a Grignard Metathesis (GRIM) polymerization method. The advantage of GRIM polymerization of thiophenes is that it provides a very high percentage of regioregularity (all side chains facing the same direction), and regioregularity leads to better planarity. Although the GRIM method for polymerizations are shown, other polymerizations known to those skilled in the art are suitable to produce polythiophenes.

In some embodiments, the polymerization produces a high percentage of regioregular polythiophenes. In some embodiments, the polymerization produces a high percentage of non-regioregular polythiophenes. Binding between regioregular polythiophenes and ciguatoxin, and binding between non-regioregular polythiophenes and ciguatoxin result in a color change.

In an embodiment and as shown in FIG. 9A, polythiophenes 701 (P1) and 702 (P2) may be synthesized by the following procedure. In FIGS. 9A and 9B, each R is independently alkyl or substituted alkyl, and may comprise any alkyl group or substituted alkyl as defined previously, each of X and X' is independently hydrogen or bromine; y is an integer between 1 and 17; m is an integer between 8 and 1200; and n is an integer between 8 and 1200. To a stirring solution of 2,5-dibromothiophene monomers 807 or 817 (10 mmol) in anhydrous THF (80 ml) is added a tert-butyl magnesium chloride solution (tBuMgCl, 10 mmol), dropwise. Methyl magnesium bromide (MeMgBr) may be used instead of tBuMgCl. The solution is heated to about reflux and stirred for about 2 hours before [1,3-Bis(diphenylphosphino)propane]dichloronickel(II) (Ni(dppp)$Cl_2$, 27 mg, 0.05 mmol) is added. The mixture is stirred for at least about 1 hour and poured into methanol (200 ml). The solid polymer is filtered as purified via Soxhlet extraction using subsequent washes with methanol, hexane, and chloroform. The solvent from chloroform fraction was removed in vacuo and the solid polymer is dried in vacuo to provide either polythiophene 701 (P1) or polythiophene 702 (P2).

In an embodiment and as shown in FIG. 9B, polythiophenes 703 (P3) and 704 (P4) may be synthesized by the following procedure. To a stirring solution of 2,5-dibromothiophene monomers 807 or 817 and dibrom-3-alkylthiophene 901 (combined total of 10 mmol) in anhydrous THF (80 ml) is added a tert-butyl magnesium chloride solution (tBuMgCl, 10 mmol), dropwise. Methyl magnesium bromide (MeMgBr) may be used instead of tBuMgCl. Dibromoalkylthiophene 901 (R=alkyl or substituted alkyl) may comprise any alkyl group or substituted alkyl as defined previously. In addition, alkyl group and substituted alkyl group can include ethylene glycol functionality, and/or ethylene oxide side chains. The solution is heated to about reflux and stirred for about 2 hours before [1,3-Bis(diphenylphosphino)propane]dichloronickel(II) (Ni(dppp)$Cl_2$, 27 mg, 0.05 mmol) is added. The mixture is stirred for at least about 1 hour and poured into methanol (200 ml). The solid polymer is filtered as purified via Soxhlet extraction using subsequent washes with methanol, hexane, and chloroform. The solvent from chloroform fraction was removed in vacuo and the solid polymer is dried in vacuo to provide either polythiophene 703 (P3) or polythiophene 704 (P4).

The method 500 of forming a detectable composition includes forming a functionalized polythiophene at operation 520. This operation involves transforming the ester of any of polythiophenes 701 (P1)-704 (P4) to an acid chloride 701' (P1')-704' (P4') via saponification and chlorination according to some embodiments.

Figure 10A:
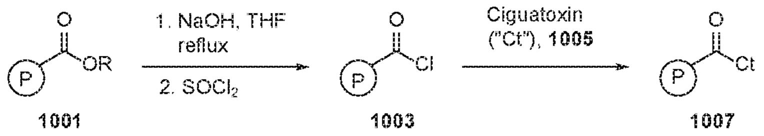
FIG. 10A shows the synthesis of exemplary functionalized polythiophene compounds and their reaction with ciguatoxin.

In an embodiment and as shown in FIG. 10A, a polythiophene 1001 ("P" represents polythiophenes 701 (P1)-704 (P4)) is converted to acid chloride 1003 according to the following procedure. To a stirring solution of polythiophene (P1-P4) (5 mmol) and tetrabutylammonium bromide (5 mol %) in 25 mL THF, toluene, or chloroform is added an aqueous solution of 1.0M NaOH (25 ml). Aqueous LiOH or KOH may be used instead of NaOH. The mixture is heated to about reflux and stirred for about 6 hours. The solution is poured into methanol, filtered, and the polymer is rinsed with methanol followed by excess water. The polymer is dried in vacuo to provide a polythiophene having a carboxylic acid group (not shown).

To a stirring solution of the polythiophene having an acid group (5 mmol) in 25 ml THF, toluene, or dichloromethane is added thionyl chloride ($SOCl_2$, 20 mmol). The mixture is heated to about reflux and stirred for about 2 hours. The solution is poured into dry acetone, diethyl ether, or hexane. The resulting precipitate is filtered, and the polymer was rinsed with additional solvent (acetone, diethyl ether, or hexane). The polymer was dried in vacuo, providing a functionalized polythiophene 1003 (representing 701' (P1')-704' (P4')).

Figure 10B:
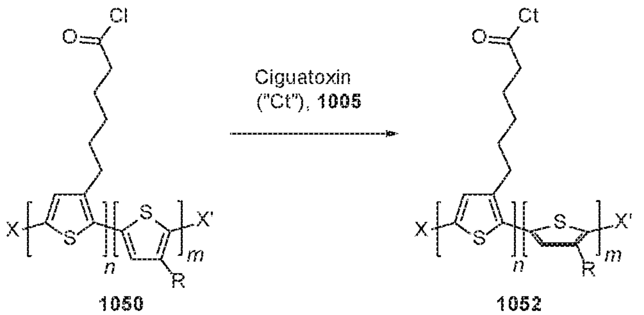
FIG. 10B shows the reaction of an exemplary functionalized polythiophene compound and its reaction with ciguatoxin.

In FIGS. 10A and 10B, each R is independently alkyl or substituted alkyl, and may comprise any alkyl group or substituted alkyl as defined previously, each of X and X' is independently hydrogen or bromine; m is an integer between 8 and 1200; and n is an integer between 8 and 1200.

Method 500 includes obtaining a material comprising a target substance at operation 525. In some embodiments, the target substance is ciguatoxin. It is contemplated that other toxins and target substances (and their metabolites) bearing a primary hydroxyl group can be detected. It is also contemplated that other biotoxins, chemical compounds, or other contaminants indicative of aquatic stress can be identified. The material comprising the toxic substance includes any material containing a toxin, such as seafood, fish, aquatic invertebrates, tissue samples, samples that are macerated and extracted in a suitable solvent, water samples, plant samples, and other aquatic samples.

Method 500 includes reacting the material comprising the target substance with the functionalized polythiophene compound to form a functionalized target substance at operation 530 according to some embodiments. For example, the target substance is ciguatoxin ("Ct") 1005 and the functionalized polythiophene compound is the acyl chloride 1003 as shown in FIG. 10A. In this example, the primary hydroxyl of ciguatoxin ("Ct") reacts with the chloride of the functionalized polythiophene compound to form a functionalized ciguatoxin 1007 (or other substance to be detected). As shown in FIG. 10B, introduction of ciguatoxin to a functionalized polythiophene (for example, y=5, X=H, X'=Br) 1050 results in reaction with the acid chloride, which disrupts the planarity of the conjugated polythiophene backbone (see polythiophene 1052) and causes a blue-shifted color change.

It should be noted that one or more of the operations may occur before or after that shown in FIG. 5 or may occur simultaneously in some embodiments. For example, operations 505 through 520 may occur after operation 515.

FIG. 6 illustrates a method 600 for detecting a target substance, for example ciguatoxin, according to some embodiments. It is contemplated that other toxins and target substances (and their metabolites) bearing a primary hydroxyl group can be detected. It is also contemplated that other biotoxins, chemical compounds, or other contaminants indicative of aquatic stress can be identified.

At operation 605, a sample is macerated and extracted in a suitable first solvent in which the target substance is soluble. This first solvent is an oil that is liquid at about room temperature (between about 15° C. and about 25° C.). Examples of the first solvent include liquid triglycerides (such as vegetable oil, olive oil, linseed oil, flax seed oil, and combinations thereof) and fatty acids that are liquids at room temperature. The first solvent may be a nonpolar solvent such as heptane, naptha, xylene, toluene, $CH_2Cl_2$. This operation may involve mechanical stirring, sonic agitation, chemical extraction, etc. The extract may optionally be filtered. The sample includes any material containing a toxin, such as seafood, fish, aquatic invertebrates, tissue samples, samples that are macerated and extracted in a suitable solvent, water samples, plant samples, and other aquatic samples.

To the extract is added an empirically determined quantity of first compound (e.g., a first functionalized polythiophene compound) to form a first mixture at operation 610. The first compound is a polythiophene bearing an acid chloride (or an acid bromide). The first compound may be any polythiophene that acts as a chromophore. The first compound may be added as a solution in an organic solvent such as dichloromethane, chloroform, tetrahydrofuran, dimethylformamide, and toluene from an ampule, or the first compound may be placed in a matrix such as polyethylene glycol (PEG), or a polyethylene glycol-polymethyl methacrylate (PEG-PMMA).

In some embodiments, the first compound (e.g., the first functionalized polythiophene compound) is placed in a polymer matrix. For example, a desired ratio of the first compound and a polymer are dissolved in a cosolvent such as THF, benzene, $CH_2Cl_2$, chloroform, 1,4-dioxane, or combinations thereof, and a thin layer of the resultant material may be coated onto a surface and allowed to dry under ambient conditions. The mixture of first compound and polymer matrix may optionally include additives.

Alternately, and in order to affect miscibility between the first compound and the polymer matrix, the R groups of the first compound can be utilized. For example, polythiophenes 703, 704, 703', and 704' may have an R group miscible with polyethylene glycol (PEG) such as an ethylene glycol group or ethylene oxide group. A desired ratio of this functionalized polythiophene and a polymer are then dissolved in a cosolvent such as THF, benzene, $CH_2Cl_2$, chloroform, 1,4-dioxane, or combinations thereof, and a thin layer of the resultant material may be coated onto a surface and allowed to dry under ambient conditions. The mixture of first compound and polymer matrix may optionally include additives.

The first mixture is allowed to react for an empirically determined time at an empirically determined temperature to form a second mixture comprising a second compound (e.g., a second functionalized polythiophene compound) at operation 615. The temperature and time will depend on the reactivity of the first compound. In an embodiment and as described above, acid chloride functionalized polythiophene 1003 is the first compound. The first compound reacts with the target substance (e.g., ciguatoxin) in the extract to form the second compound. The second compound may be represented by, for example, polythiophene compound 1007 and polythiophene compound 1052.

In some embodiments, an optional operation of removing the unreacted materials (i.e., first compound) may be performed. This operation depends on the precise characteristics of the materials. Extracting with a solvent to remove unreacted materials is one such removal method. Another method may include chromatography. These methods are discussed above.

At operation 620, a colorimetric analysis is performed on the second mixture comprising the second compound and the result correlated to a target substance concentration using a standardized absorbance curve (or color scale) prepared independent of the sample. The mixture is either observed visually or compared to a color wheel or color strip, or the absorbance is measured in a simple spectrometer and compared to a known spectra.

It should be noted that one or more of the operations may occur before or after that shown in FIG. 6 or may occur simultaneously in some embodiments. For example, operations 605 may occur after operation 615.

Kits for the Colorimetric Analysis

The disclosure also includes systems for carrying out the methods described herein according to some embodiments. Typically, a system to be used for colorimetric analysis includes a functionalized polythiophene, one or more solvents and an extraction solvents. The solvents and extraction solvents may be any solvent and extraction solvent described above.

The functionalized polythiophene may be any polythiophene that is a chromophore such as those described herein. The functionalized polythiophene reacts with the target substance. For implementation, the functionalized polythiophene may be dissolved into a solution of an organic solvent such as dichloromethane, chloroform, tetrahydrofuran, dimethylformamide, and toluene and placed in an ampule that can be opened and reacted with the fish extract. Alternately, the functionalized polythiophene may be placed in a matrix such as polyethylene glycol to which the fish extract is added.

In some embodiments, the system further comprises one or more of a container, a color wheel, a color strip, simple spectrometer, and reference spectra. In some embodiments, a heat source is provided. The heat source may include any suitable heating apparatus including a hot lamp and a heating mantle.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing is directed to embodiments of the present invention, other and further embodiments of the invention may be devised without departing from the basic scope thereof, and the scope thereof is determined by the claims that follow.

What is claimed is:

1. A method for detecting a target substance, comprising:
macerating and extracting a sample to produce an extract, the extract comprising the target substance;
providing a first mixture comprising the extract and a first polymerizable compound comprising a substituent that reacts with a primary hydroxyl group;
reacting the first polymerizable compound with the extract to form a second mixture comprising a second polymerizable compound;
extracting the second mixture with a solvent;
adding a thermal initiator to the second mixture comprising the second polymerizable compound;
performing a polymerization reaction on the second mixture comprising the second polymerizable compound to form a third mixture comprising a precipitate; and
performing a turbidimetric analysis on the third mixture comprising the precipitate.

2. The method of claim 1, wherein the performing a polymerization reaction comprises exposing the second mixture to radiation.

3. The method of claim 2, wherein the radiation is thermal radiation.

4. The method of claim 1, wherein the target substance comprises ciguatoxin.

5. The method of claim 1, wherein the first polymerizable compound is a multifunctional compound comprising an acrylate, methacrylate, acrylamide, methacrylamide, vinyl acetate, vinyl formamide, epoxide, aldehyde, halohydrins, disulfonate esters, esters, acid halides, carboxylic acids, carboxylic acid anhydrides, melamine resins, hydroxymethyl ureas, isocyanates, thioethers, or combinations thereof.

6. The method of claim 1, wherein the first polymerizable compound is a derivative of dipentaerythritol pentaacrylate.

7. The method of claim 1, wherein the thermal initiator comprises benzopinacol, tert-amyl peroxybenzoate, 1,1'-azobis(cyclohexanecarbonitrile), 2,2'-azobisisobutyronitrile (AIBN), 2,2-bis(tert-butylperoxy)butane, 1,1-bis(tert-butylperoxy)cyclohexane, 2,5-bis(tert-butylperoxy)-2,5-dimethylhexane, 2,5-bis(tert-butylperoxy)-2,5-dimethyl-3-hexyne, bis(1-(tert-butylperoxy)-1-methylethyl)benzene, 1,1-bis(tert-butylperoxy)-3,3,5-(dibutyl phthalate)trimethylcyclohexane, tert-butyl hydroperoxide, tert-butyl peracetate, tert-butyl peroxide, tert-butyl peroxybenzoate, tert-butylperoxy isopropyl carbonate, cumene hydroperoxide, cyclohexanone peroxide, dicumyl peroxide, lauroyl peroxide, peracetic acid, or combinations thereof.

8. A method for detecting a target substance, comprising:

macerating and extracting a sample to produce an extract, the extract comprising the target substance;

providing a first mixture comprising the extract and a first polymerizable compound comprising a substituent that reacts with a primary hydroxyl group wherein the first polymerizable compound is a derivative of dipentaerythritol pentaacrylate;

reacting the first polymerizable compound with the extract to form a second mixture comprising a second polymerizable compound;

adding an initiator to the second mixture comprising the second polymerizable compound;

performing a polymerization reaction on the second mixture comprising the second polymerizable compound to form a third mixture comprising a precipitate, wherein the performing a polymerization reaction comprises exposing the second mixture to radiation; and performing a turbidimetric analysis on the third mixture comprising the precipitate.

9. The method of claim 8, further comprising extracting the second mixture with a solvent.

10. The method of claim 8, wherein the radiation is ultraviolet (UV) radiation.

11. The method of claim 8, wherein the radiation is thermal radiation.

12. The method of claim 8, wherein the initiator is a photoinitiator, a thermal initiator, or a combination thereof.

13. The method of claim 8, wherein the target substance comprises ciguatoxin.

14. A method for detecting a target substance, comprising:

macerating and extracting a sample to produce an extract, the extract comprising ciguatoxin;

providing a first mixture comprising the extract and a first polymerizable compound comprising a substituent that reacts with a primary hydroxyl group;

reacting the first polymerizable compound with the extract to form a second mixture comprising a second polymerizable compound;

adding an initiator to the second mixture comprising the second polymerizable compound;

performing a polymerization reaction on the second mixture comprising the second polymerizable compound to form a third mixture comprising a precipitate, wherein the performing a polymerization reaction comprises exposing the second mixture to radiation; and performing a turbidimetric analysis on the third mixture comprising the precipitate.

15. The method of claim 14, further comprising extracting the second mixture with a solvent.

16. The method of claim 14, wherein the radiation is ultraviolet (UV) radiation.

17. The method of claim 14, wherein the radiation is thermal radiation.

18. The method of claim 14, wherein the initiator is a photoinitiator, a thermal initiator, or a combination thereof.

19. The method of claim 18, wherein the thermal initiator comprises benzopinacol, tert-amyl peroxybenzoate, 1,1'-azobis(cyclohexanecarbonitrile), 2,2'-azobisisobutyronitrile (AIBN), 2,2-bis(tert-butylperoxy)butane, 1,1-bis(tert-butylperoxy)cyclohexane, 2,5-bis(tert-butylperoxy)-2,5-dimethylhexane, 2,5-bis(tert-butylperoxy)-2,5-dimethyl-3-hexyne, bis(1-(tert-butylperoxy)-1-methylethyl)benzene, 1,1-bis(tert-butylperoxy)-3,3,5-(dibutyl phthalate)trimethylcyclohexane, tert-butyl hydroperoxide, tert-butyl peracetate, tert-butyl peroxide, tert-butyl peroxybenzoate, tert-butylperoxy isopropyl carbonate, cumene hydroperoxide, cyclohexanone peroxide, dicumyl peroxide, lauroyl peroxide, peracetic acid, or combinations thereof.

20. The method of claim 14, wherein the first polymerizable compound is a multifunctional compound comprising an acrylate, methacrylate, acrylamide, methacrylamide, vinyl acetate, vinyl formamide, epoxide, aldehyde, halohydrins, disulfonate esters, esters, acid halides, carboxylic acids, carboxylic acid anhydrides, melamine resins, hydroxymethyl ureas, isocyanates, thioethers, or combinations thereof.

* * * * *